United States Patent
Gupta et al.

(10) Patent No.: US 12,251,537 B2
(45) Date of Patent: Mar. 18, 2025

(54) SYRINGE SYSTEM FOR FLUID SEPARATION

(71) Applicant: Board of Trustees of Southern Illinois University, Springfield, IL (US)

(72) Inventors: Ashim Gupta, Lawrenceville, GA (US); Michael W. Neumeister, Springfield, IL (US); Sohyung Cho, Maplewood, MO (US); Scott Moore, Chatham, IL (US); Robert B. Zajeski, Jr., Crete, IL (US)

(73) Assignee: Board of Trustees of Southern Illinois University, Springfield, IL (US)

( * ) Notice: Subject to any disclaimer, the term of this patent is extended or adjusted under 35 U.S.C. 154(b) by 1070 days.

(21) Appl. No.: 16/984,605

(22) Filed: Aug. 4, 2020

(65) Prior Publication Data
US 2020/0360609 A1    Nov. 19, 2020

Related U.S. Application Data

(63) Continuation-in-part of application No. 15/645,657, filed on Jul. 10, 2017, now Pat. No. 10,774,301.

(60) Provisional application No. 62/360,550, filed on Jul. 11, 2016.

(51) Int. Cl.
| | | |
|---|---|---|
| A61M 5/19 | (2006.01) | |
| A61M 5/315 | (2006.01) | |
| A61M 5/32 | (2006.01) | |
| C12M 1/00 | (2006.01) | |

(52) U.S. Cl.
CPC .......... *A61M 5/19* (2013.01); *A61M 5/31511* (2013.01); *A61M 5/3213* (2013.01); *C12M 47/04* (2013.01)

(58) Field of Classification Search
None
See application file for complete search history.

(56) References Cited

U.S. PATENT DOCUMENTS

| | | | | |
|---|---|---|---|---|
| 2005/0123895 A1* | 6/2005 | Freund | ............... | B01D 17/0217 436/164 |
| 2010/0249753 A1* | 9/2010 | Gaisser | ............... | B01F 33/5011 604/519 |
| 2011/0166596 A1* | 7/2011 | Delmotte | .............. | A61J 1/2093 606/214 |
| 2012/0136298 A1* | 5/2012 | Bendix | ............. | A61M 5/31515 29/428 |

* cited by examiner

Primary Examiner — Matthew D Krcha
Assistant Examiner — Brittany I Fisher
(74) *Attorney, Agent, or Firm* — Robert M. Patino

(57) ABSTRACT

A syringe device and methods for device for separating liquids of different densities are provided where the syringe device includes a hollow syringe barrel, a perforated plunger seal with a seal hole, and a hollow plunging tube with a closed bottom with at least one tube hole.

20 Claims, 12 Drawing Sheets

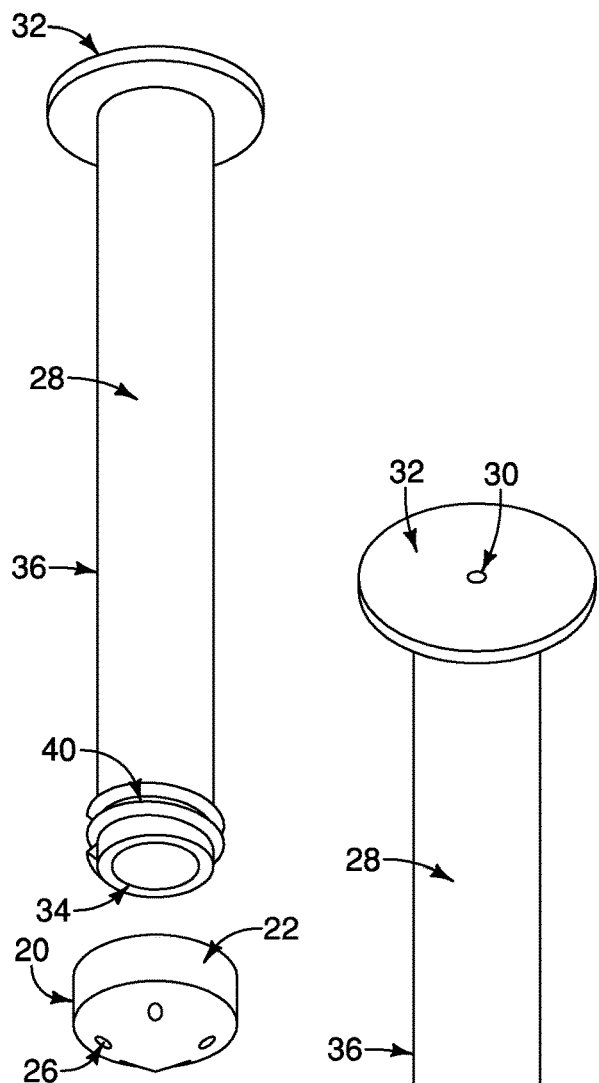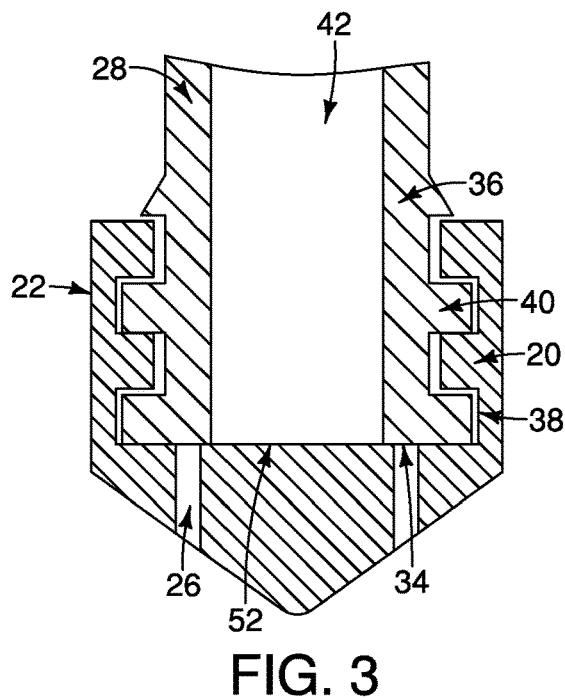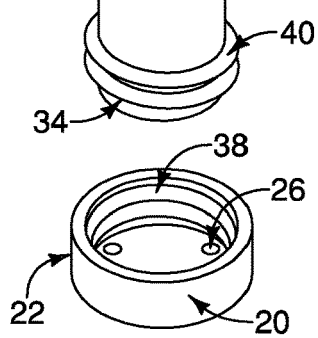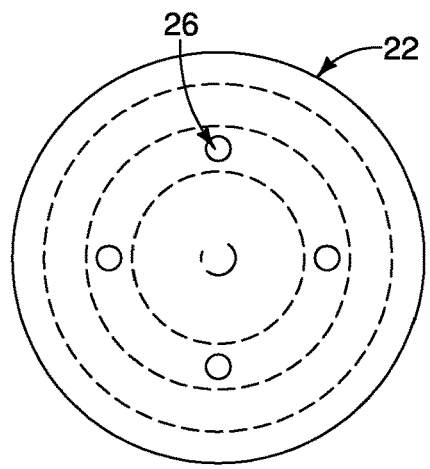
FIG. 1
FIG. 2
FIG. 3
FIG. 4

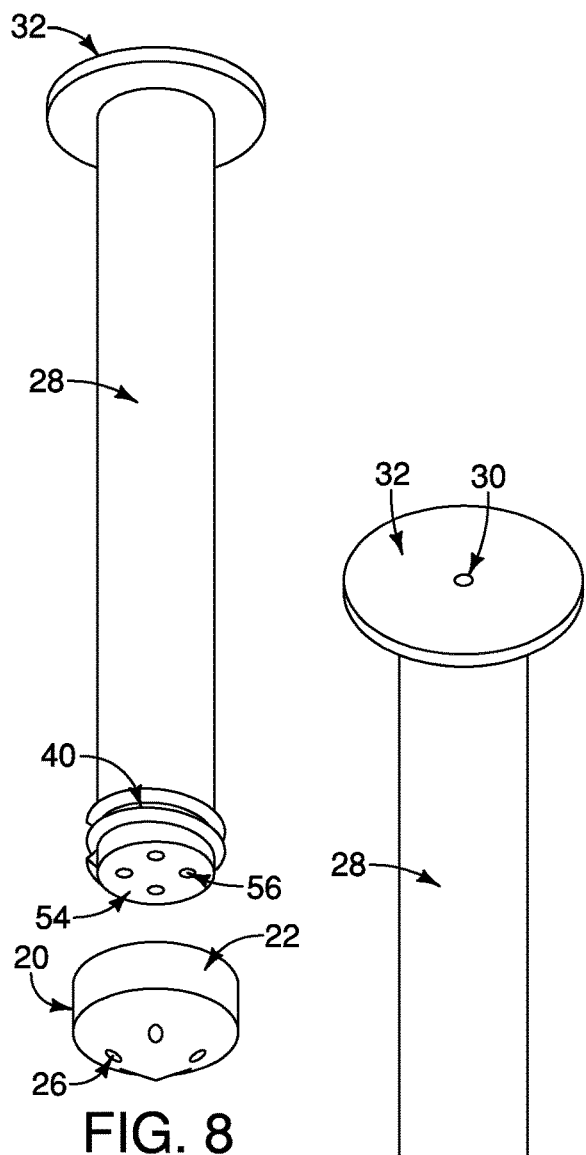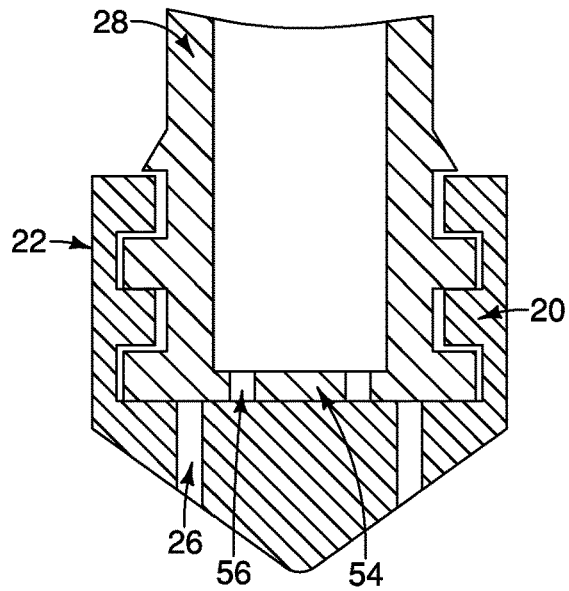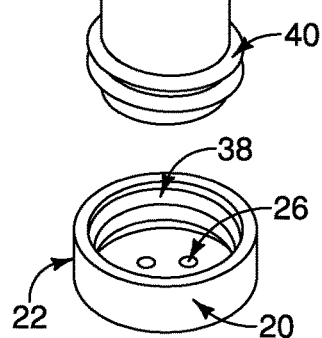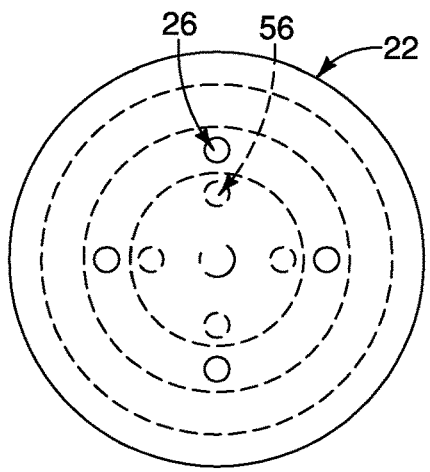
FIG. 8
FIG. 10
FIG. 9
FIG. 11

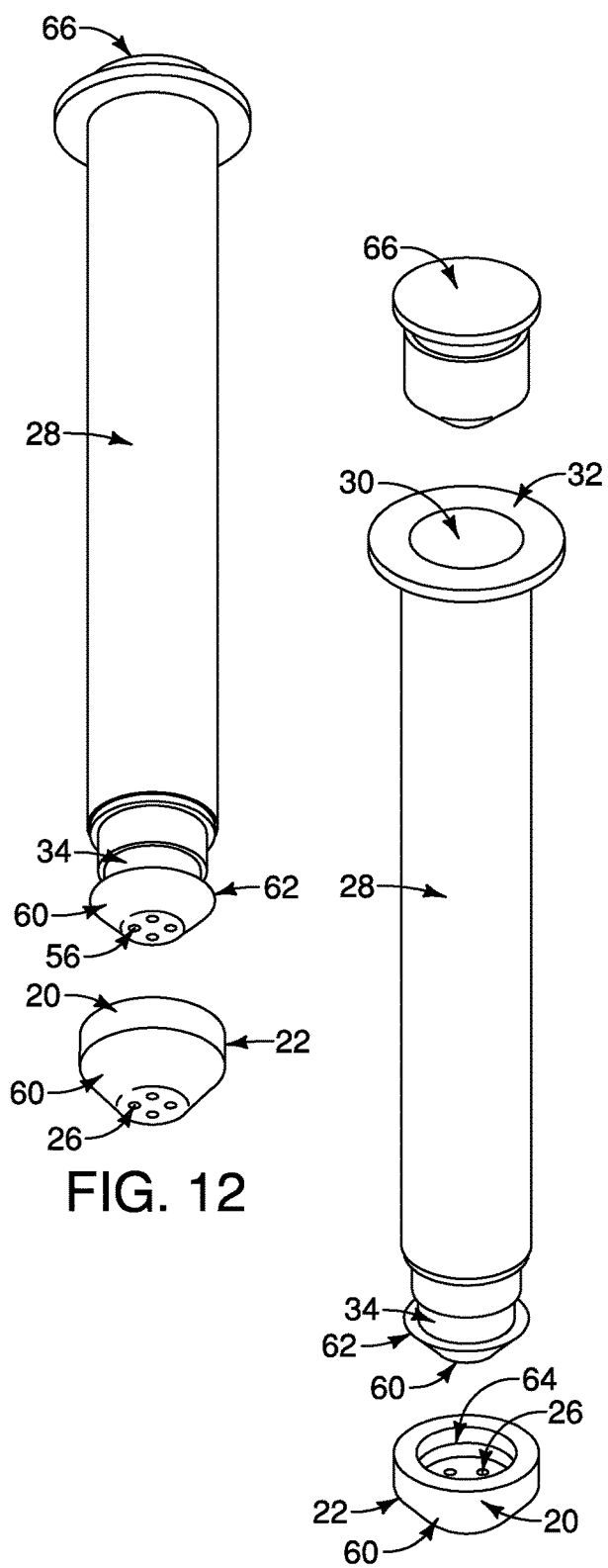
FIG. 12
FIG. 13
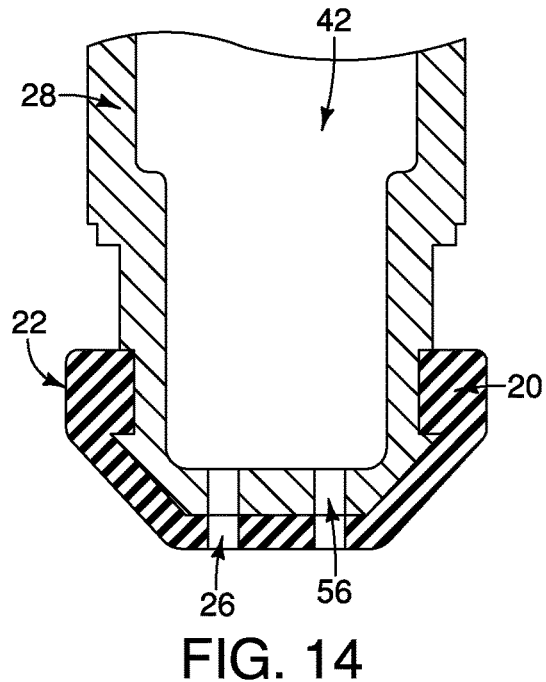
FIG. 14
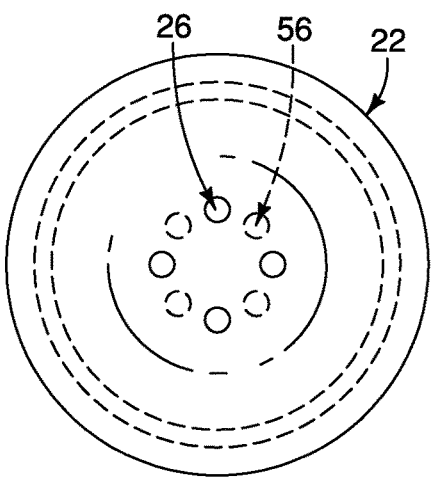
FIG. 15

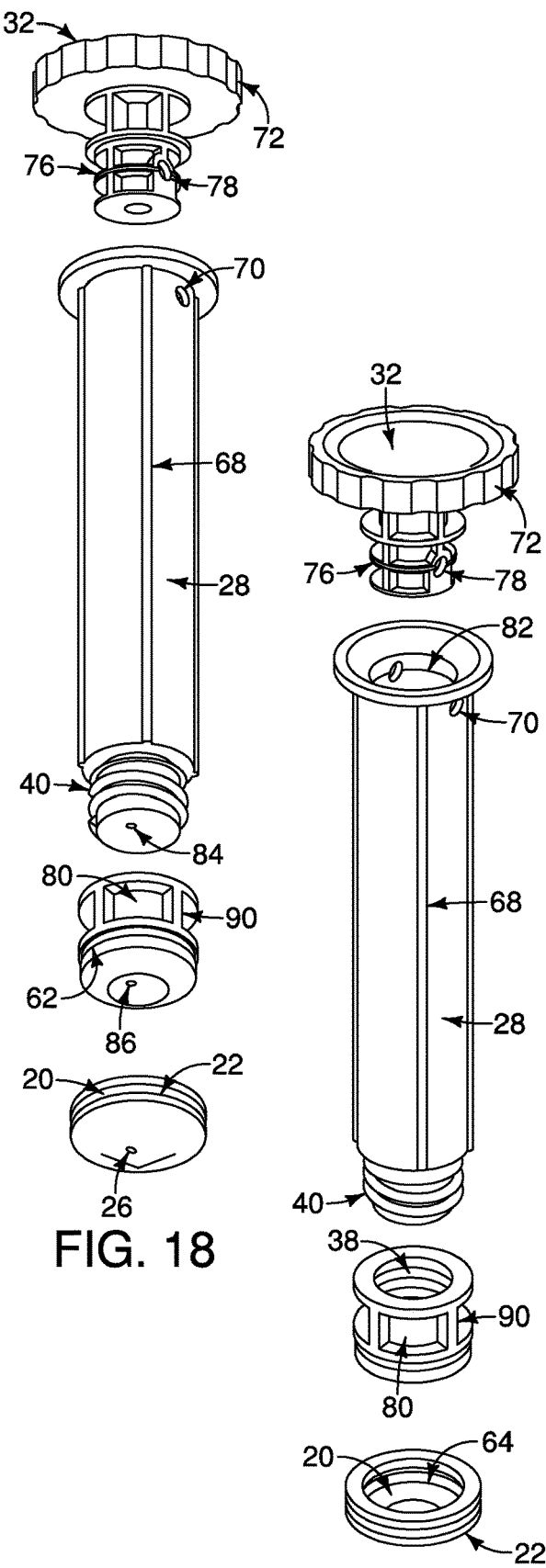
FIG. 18
FIG. 19
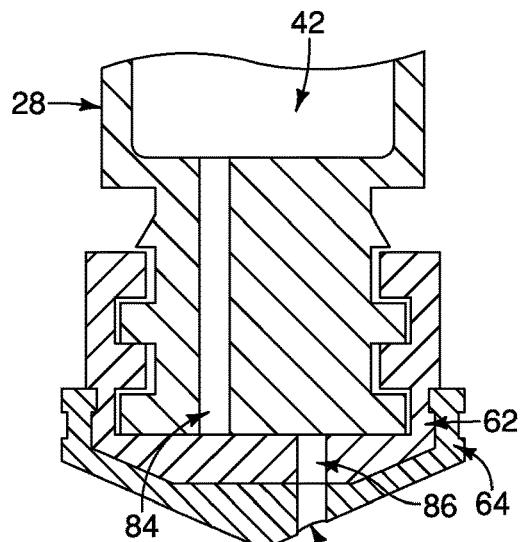
FIG. 20
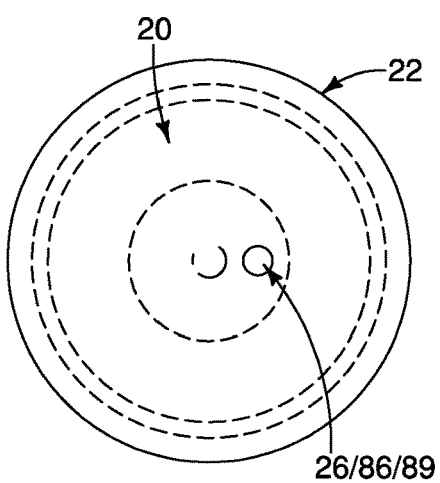
FIG. 21

SYRINGE SYSTEM FOR FLUID SEPARATION

CROSS-REFERENCE TO RELATED APPLICATION

This application is a continuation-in-part of co-pending U.S. patent application Ser. No. 15/645,657, filed Jan. 10, 2017, entitled "Novel Syringe System for Fluid Separation," which relates to and claims priority to U.S. provisional patent application Ser. No. 62/360,550 filed on Jul. 11, 2016. The disclosure of each of the above-reference patent applications is expressly incorporated herein in its entirety.

BACKGROUND OF THE INVENTION

Autologous fat transfer, also known as fat grafting, has emerged as a widely used breast and facial reconstruction technique. Lipofilling, a form of fat grafting, has been used for several years, for example, to repair minor differences between a reconstructed breast and the non-reconstructed breast or to fill large dents in the body or face. Further uses include clinical applications to treat scleroderma, post-radiation skin damage, and skin rejuvenation. A surgeon performing a lipofilling procedure must go through several steps to obtain the fat cells necessary for grafting. After initial extraction by vacuum suction of raw lipoaspirate from the patient, the fat cells must be separated from the blood, debris, and oil in the lipoaspirate mixture.

One way to accomplish separation of fat cells is to allow gravity to separate out the layers naturally. This can be a slow, time-consuming process, taking approximately twenty to thirty minutes to achieve appropriate separation. Once separated, multiple syringes and other containers are employed to fully isolate the fat.

Another method to accomplish separation is by placing the suctioned fat in a cloth and squeezing the fat or allowing it to drain until the impurities are removed. This method is problematic because it is a complicated procedure, is time-consuming, and there is a greater risk of the fat cells becoming infected due to contact with the environment.

Still another method of separation is accomplished by placing the syringe in a centrifuge. The centrifuge rotates at approximately 1000 rpm for two to three minutes, allowing three layers to form: a more-dense blood and debris layer on the bottom, a desired fat cell layer in the middle, and a less-dense oil layer on top. Once separated, multiple syringes and containers must typically be employed to isolate the desired fat cells before the desired fat cells can be grafted back into the patient.

Methods of removing the oil layer from lipoaspirate solutions separated by gravity or centrifugation without the use of multiple containers and syringes remain inefficient and burdensome. The oil is trapped above the fat layer and cannot be discharged from conventional syringes or containers without prolonged effort. Each separation technique of the lipoaspirate that occurs in any of the above methods decreases the efficacy of the treatment as a whole for myriad reasons. Exposure of fat cells to potential contaminants or unnecessary trauma lead to an increase in potential infection or cell necrosis. Either of these conditions can cause serious complications in the patient or require further treatment to correct any issues. Potential risks to patient under sedation are also of concern. Typically, the longer a patient is under anesthesia, the greater the potential risk to a patient for an anesthesia-associated complication to occur.

As such, there is a need to reduce the required active steps involved in harvesting fat cells to increase the effectiveness, safety, and efficiency of the procedure. Fewer active steps would enhance the likelihood of the healthy fat cells being successfully grafted, reduce potential patient harm, and shorten the procedure to reduce the costs associated with the treatment.

BRIEF SUMMARY OF THE INVENTION

The abovementioned needs are solved by the present invention, which leverages a syringe system, preferably in combination with centrifugation, to enable fast liquid phase separation that allows the desired fat cells to be grafted into the body more quickly and with lower risk of contamination or fat cell damage. The present invention improves the separation and isolation of liquids with varying densities via a number of features. One such feature includes a means of separating liquids of different densities by allowing the less-dense liquids that form the top layer(s) of a separated solution to pass through a controllable opening in the device, effectively isolating the top layer(s) without having to use multiple syringes. Another feature includes the ability to keep separated liquids apart without exposing them to an outside environment. An additional feature includes a means of keeping the separated liquids from mixing as the desired liquids are returned to the host. As such, various embodiments are presented that improve the ability to separate fat cells from the oil layer in a separated lipoaspirate solution without having to use multiple containers and without further exposing the fat cells to the outside environment. It is also noted that this invention may be used in a similar manner for liquid solutions that contain varying densities (such as whole blood or hazardous waste) and is not intended to be limiting to lipoaspirate solutions.

In a first embodiment, a syringe device for separating liquids of different densities is provided with a hollow syringe barrel, a hollow plunging tube that is insertable into the hollow syringe barrel, and a perforated plunger seal that resides flush against an interior surface of the hollow syringe barrel when the plunging tube is inserted into the hollow syringe barrel. The perforated plunger seal has at least one seal hole that extends through the perforated plunger seal. A wall of the hollow plunging tube resides above the perforated plunging seal when the discharge opening is pointed down and is in operational relationship to the at least one seal hole. The term "above" here and throughout assumes a frame of reference where the end of the hollow syringe barrel that receives the hollow plunging tube is pointed upward and the end of the hollow plunging tube that connects to the perforated plunging seal is pointed downward. The hollow plunging tube is threadably coupled to the perforated plunger seal. When set to an open position, the seal hole allows liquids to flow from a hollow syringe barrel cavity into a hollow plunging tube cavity.

In a second embodiment, a syringe device for separating liquids of different densities is provided with a hollow syringe barrel, a hollow plunging tube with a sealed bottom, and a perforated plunger seal that resides flush against an interior surface of the hollow syringe barrel. The hollow plunging tube with a sealed bottom has at least one tube hole in the sealed bottom and the perforated plunger seal has at least one seal hole. The hollow plunging tube and perforated plunger seal are threadably connected by a male interlocking thread on the bottom portion of the hollow plunging tube and a female interlocking thread on the perforated plunger seal.

A relief hole is optionally located on or near the top portion of the hollow plunging tube to provide for a vacuum as necessary.

In a third embodiment, a syringe device for separating liquids of different densities is provided with a hollow syringe barrel, a hollow plunging tube with a sealed bottom, and a perforated plunger seal that resides flush against an interior surface of the hollow syringe barrel. The perforated plunger seal has at least one seal hole. The hollow plunging tube with a sealed bottom is provided with at least one tube hole that passes through the sealed bottom. Then at least one tube hole is in operational relationship with the at least one seal hole of the perforated plunger seal. The hollow plunging tube and the perforated plunger seal are flushly coupled by a lip on the hollow plunging tube with the sealed bottom.

In a fourth embodiment, a syringe device for separating liquids of different densities is provided with a hollow syringe barrel and a perforated plunger seal that resides flush against an interior surface of the hollow syringe barrel. The perforated plunger seal has at least one seal hole. A bottom portion adapter is further provided that has an at least one bottom portion adapter hole that corresponds with the at least one seal hole in said perforated plunger seal. Portions of the bottom portion adapter reside flush against the perforated plunger seal. A hollow plunging tube with a sealed bottom is also provided and resides in operational relationship with the bottom portion adapter. The hollow plunging tube has an at least one tube hole, a relief hole, and a top portion.

In a fifth embodiment, a syringe device for separating liquids of different densities is provided with a hollow syringe barrel and a perforated plunger seal. The perforated plunger seal has an inner and outer perimeter. The outer perimeter of the perforated plunger seal resides flush against an interior surface of the hollow syringe barrel. The perforated plunger seal has an at least one seal hole. A bottom portion adapter is further provided that has an at least one bottom portion adapter hole that corresponds with the at least one seal hole in said perforated plunger seal. Portions of the bottom portion adapter reside flush against the perforated plunger seal. A hollow plunging tube with a sealed bottom is also provided that resides in operational relationship with the bottom portion adapter. The hollow plunging tube has a bottom portion rotatable from an open position and a closed position. The bottom portion contains a bottom opening which faces the interior of the bottom portion adapter. A removable stop cap with at least one top portion relief hole resides in operational relationship with the top portion of the hollow plunging tube. The bottom portion adapter optionally includes an at least one bottom portion adapter guide rail and the hollow plunging tube optionally includes an at least one hollow plunging tube guide peg that aligns inside an at least one bottom portion adapter guide rail.

In an optional embodiment, the disclosure herein provides for a method of separating a light density fluid, a middle density fluid and a heavy density fluid from a sample containing a mixture of each. The method includes extracting the sample from a subject by pulling a hollow plunging tube in a reverse manner until a hollow syringe barrel is filled with the sample; placing a needle stop cap at a beveled needle hub on the hollow syringe barrel; using a separating force such that the heavy density fluid is forced to the bottom of the hollow syringe barrel; rotating the removable stop cap until at least one top portion relief hole on the removable stop cap is in an unsealed position and rotating the hollow plunging tube until the bottom portion adapter is in an open position; filling the hollow plunging tube with substantially all of the light density fluid by pushing the hollow plunging tube in a forward manner; rotating the hollow syringe barrel until the bottom portion adapter is in a closed position; removing the needle stop cap from the beveled needle hub and pushing the hollow plunging tube in a forward manner. Optionally, the hollow plunging tube may be pushed forward until substantially all of the heavy density fluid is removed from the hollow syringe barrel.

The disclosure herein further provides an alternative method of separating a light density fluid, a middle density fluid and a heavy density fluid from a sample containing a mixture of each. The method includes extracting the sample from a subject by pulling the hollow plunging tube in a reverse manner until the hollow syringe barrel is filled with the sample; placing a needle stop cap at a beveled needle hub on the hollow syringe barrel; removing the hollow plunging tube from the bottom portion adapter; placing a temporary stop cap in operational relationship with the bottom portion adapter; using a separating force such that the heavy density fluid is forced to a bottom of the hollow syringe barrel; removing the temporary stop cap; placing the hollow plunging tube in operational relationship with the bottom portion adapter and the removable stop cap; rotating the removable stop cap until at least one top portion relief hole on the removable stop cap is in an unsealed position and rotating the hollow plunging tube until the bottom portion adapter is in an open position; filling the hollow plunging tube with substantially all of the light density fluid by pushing the hollow plunging tube in a forward manner; rotating the hollow syringe barrel until the bottom portion adapter is in a closed position; removing the needle stop cap from the beveled needle hub and pushing the hollow plunging tube in a forward manner.

DESCRIPTION OF THE DRAWINGS

FIG. 1 illustrates a bottom-up, side perspective view of a hollow plunging tube and a corresponding perforated plunger seal in a first embodiment.

FIG. 2 illustrates a top-down, side perspective view of the hollow plunging tube and the corresponding perforated plunger seal in the first embodiment.

FIG. 3 illustrates a cross-sectional view of a bottom portion of the hollow plunging tube and the corresponding perforated plunger seal in a closed position in the first embodiment.

FIG. 4 illustrates a planar view from a bottom perspective of the perforated plunger seal and the hollow plunging tube in the first embodiment.

FIG. 8 illustrates a bottom-up, side perspective view of the hollow plunging tube and the corresponding perforated plunger seal in a second embodiment.

FIG. 9 illustrates a top-down, side perspective view of the hollow plunging tube and the corresponding perforated plunger seal in the second embodiment.

FIG. 10 illustrates a cross-sectional view of the bottom portion of the hollow plunging tube and the corresponding perforated plunger seal in the closed position in the second embodiment.

FIG. 11 illustrates a planar view from a bottom perspective of the perforated plunger seal and hollow plunging tube in the second embodiment.

FIG. 12 illustrates a bottom-up, side perspective view of the hollow plunging tube and the corresponding perforated plunger seal for a third embodiment.

FIG. 13 illustrates a top-down, side perspective view of the hollow plunging tube, removable stop cap, and corresponding perforated plunger seal for the third embodiment.

FIG. 14 illustrates a cross-sectional view of the bottom portion of the hollow plunging tube and the corresponding perforated plunger seal in the open position for the third embodiment.

FIG. 15 illustrates a planar view from a bottom perspective of the perforated plunger seal and the hollow plunging tube for the third embodiment.

FIG. 18 illustrates a bottom-up, side perspective view of a removable stop cap, the hollow plunging tube, a bottom portion adapter, and the corresponding perforated plunger seal in a fourth embodiment.

FIG. 19 illustrates a top-down, side perspective of the removable stop cap, the hollow plunging tube, the bottom portion adapter, and the corresponding perforated plunger seal in the fourth embodiment.

FIG. 20 illustrates a cross-sectional view of a bottom portion of the hollow plunging tube, the bottom portion adapter, and the corresponding perforated plunger seal in the closed position in the fourth embodiment.

FIG. 21 illustrates a planar view from a bottom perspective of the hollow plunging tube, the bottom portion adapter, and the corresponding perforated plunger seal in the open position in the fourth embodiment.

DETAILED DESCRIPTION

Figure 7:
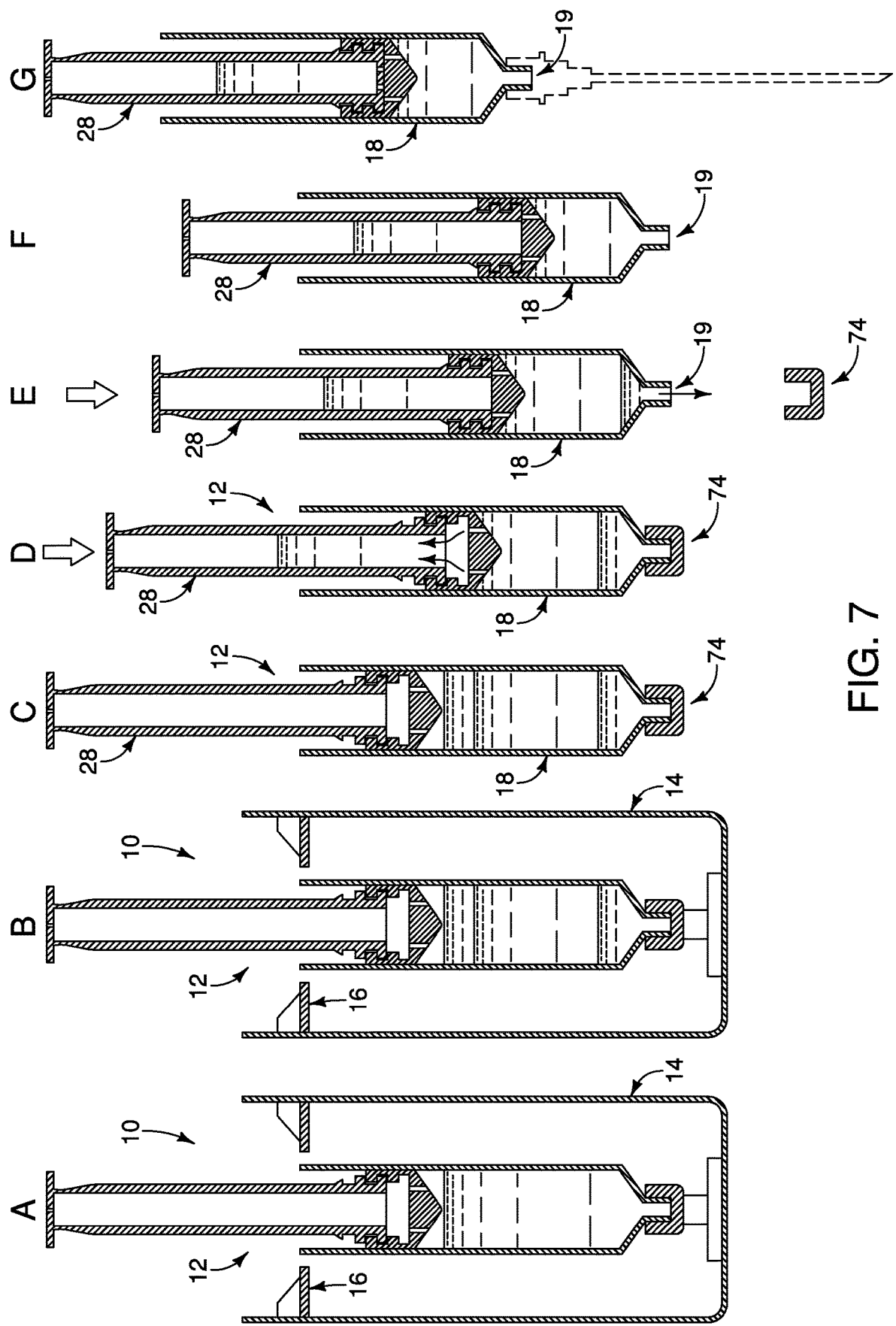
FIG. 7 illustrates the syringe system having an external tube with a support apparatus and a syringe device in the first embodiment in operation.

A syringe system 10 for separating fluids of varying densities is provided with a syringe device 12 and an optional external tube 14 as illustrated in FIG. 7. The external tube 14 is used as a holding chamber to support the syringe device 12, for instance as it goes through a spin cycle within a centrifuge (not shown). A support apparatus 16 may be used to help keep the syringe device 12 secure while the syringe device 12 is being subjected to the spin cycle. Once the liquids are separated within the syringe device 12, a process can begin to extract the separated liquid layers away from each other for use.

In one application, there is a need to isolate fat cells when fat grafting in an expedited manner. In this instance, the liquids of varying densities may be defined as oil, fat cells, and blood/debris components resulting from fat collection. When liposuction or other fat collection processes are used to remove fat from the body, a mixture is collected as shown in the first illustration of FIG. 7 and undesirable oil and debris need to be separated and removed from the fat cells. The quickest means of separating these liquids is to centrifuge the collected mixture, which creates a top oil layer (or light density liquid), a middle layer of fat cells (or middle density liquid), and a bottom blood/debris layer (or heavy density liquid) as shown in the second illustration of FIG. 7. The desired middle fat cell layer is difficult to isolate in an expedited manner. The embodiments as discussed herein illustrate varying mechanisms in which the top oil layer (or light density liquid) can be extracted from a hollow syringe barrel 18 and the bottom debris layer (or heavy density liquid) may be discharged through a discharge opening 19.

The syringe system 10 can also be used to separate multiple layers within an extracted mixture. For the exemplary application, three liquid densities are used to differentiate the separation of the collected mixture by the syringe device 12, but the syringe system may alternatively be applied to separate more than three layers. The syringe device 12 may also be operated with inverted directionality such that the light density liquid layer(s) settle adjacent to the discharge opening 19. For the purposes of maintaining continuity within the liposuction example, the syringe device as described throughout is assumed to be oriented such that the discharge opening 19 is pointed downward and the three liquid layers as described above (the top oil layer, the middle layer of fat cells, and the bottom blood/debris layer) are referred to from here and throughout as light density layer (the liquid closest to the hollow plunging tube 28), middle density layer (the liquid that does not touch the hollow plunging tube 28 nor the lower end 48 of the hollow syringe barrel 18), and heavy density layer (the liquid closest to the lower end 48 of the hollow syringe barrel 18).

Now referring to FIGS. 1-6, a first embodiment is shown and is provided with the hollow syringe barrel 18 to contain the unseparated solution or separated layer(s), as applicable given the stage of processing and isolation of the material. The hollow syringe barrel 18 is preferably made of a hard durable material such as a rigid plastic, ceramic, or metal. Also provided is a perforated plunger seal 20 with an outer perimeter 22 that resides flush against an interior surface 24 of the hollow syringe barrel 18 and is provided with an at least one seal hole 26. The perforated plunger seal 20 is preferably made of a softer, more pliable material, such as a rubber or soft plastic, to create an effective seal against the interior surface 24 of the hollow syringe barrel 18. In a preferred embodiment, 2 to 4 seal holes are used, but 1 to more than 4 seal holes may be used.

A hollow plunging tube 28 is provided that is threadably coupled to the perforated plunger seal 20. The hollow plunging tube 28 is optionally provided with an at least one relief hole 30 located on a top portion 32 of the hollow plunging tube 28. Alternatively, the at least one relief hole 30 may be located in an upper portion of the hollow plunging tube 28 as illustrated in FIG. 19, where the upper portion includes the top quarter of the hollow plunging tube 28 and includes both a wall 36 of the hollow plunging tube 28 and the top portion 32. The relief hole 30 is used to allow air to escape from the hollow plunging tube 28 as the hollow plunging tube 28 absorbs the light density liquid (fourth illustration from left in FIG. 7). A bottom portion 34 of the wall 36 of the hollow plunging tube 28 resides above and is in operational relationship to the at least one seal hole 26. An at least one female interlocking thread 38 on the perforated plunger seal 20 is aligned to correspond with an at least one male interlocking thread 40 located adjacent to the bottom portion 34 of the hollow plunging tube 28. The at least one seal hole 26 in the perforated plunger seal 20 communicates a hollow plunging tube cavity 42 within the hollow plunging tube 28 with a hollow syringe barrel cavity 44 located within the hollow syringe barrel 18 when the hollow plunging tube 28 is in an open position 50.

A beveled needle hub 46 on a lower end 48 of the hollow syringe barrel 18 allows liquids to be pushed out of the hollow syringe barrel cavity 44. During operation, a solution or material is introduced to the hollow syringe barrel cavity and the liquids of varying densities separate either through settling (e.g. gravity-assisted) or centrifugal force. The heavy density liquid settles at the bottom and can be expelled through the discharge opening 19. Once all of the heavy density liquid is removed, the middle density liquid (or in the described application, this will be the healthy fat cells) will settle within the syringe barrel cavity 44 in the lower end 48 to become the next liquid ready to be discharged from the hollow syringe barrel cavity 44.

Figure 5:
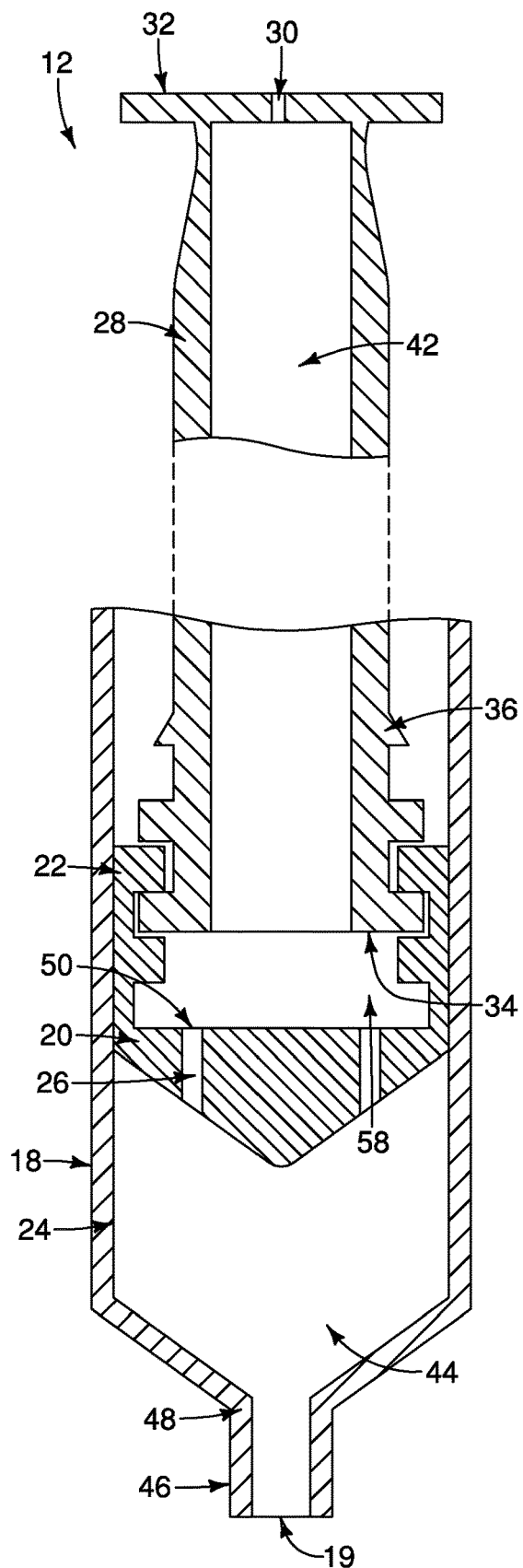
FIG. 5 illustrates a cross-sectional view of a hollow syringe barrel, the hollow plunging tube, and the corresponding perforated plunger seal set to an open position in the first embodiment.

Now referring to FIG. 5, the hollow plunging tube 28 is situated in the open position 50. This open position 50 is set prior to operation by rotating the hollow plunging tube 28 within the hollow syringe barrel 18 with respect to the perforated plunger seal 20 to set the hollow plunging tube 28 to the open position 50. In some embodiments, this rotation may be realized when the hollow plunging tube 28 and attached perforated plunger seal 20 are inserted in the hollow syringe barrel 18 by rotating the hollow plunging tube 28 with respect to the hollow syringe barrel 18, where friction between the hollow syringe barrel 18 and the perforated plunger seal 20 results in differential rotations (and thus, rotation with respect to one another) of the hollow plunging tube 28 and the perforated plunger seal 20. The at least one seal hole 26 permits liquids to flow between the hollow syringe barrel cavity 44 and the hollow plunging tube cavity 42 when the hollow plunging tube 28 is in the open position 50.

Figure 6:
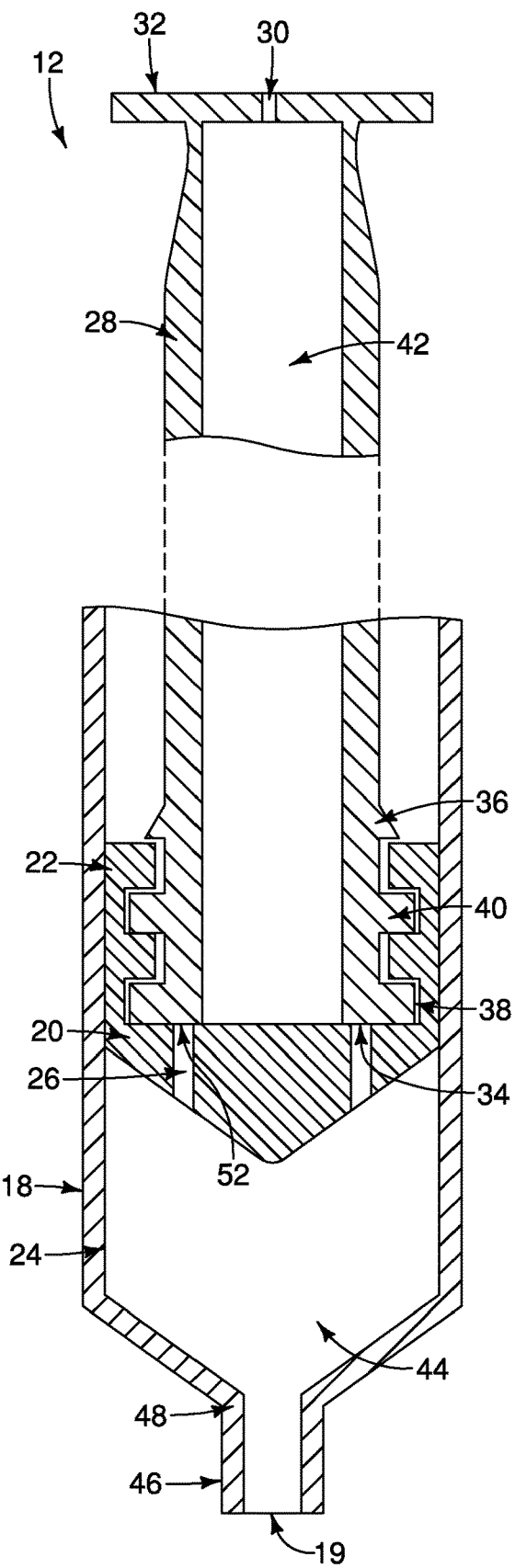
FIG. 6 illustrates a cross-sectional view of the hollow syringe barrel, the hollow plunging tube, and the corresponding perforated plunger seal set to a closed position in the first embodiment.

Now referring to FIGS. 3 and 6, the hollow plunging tube 28 is rotated to set the hollow plunging tube 28 to a closed position 52. In the closed position 52, the at least one seal hole 26 is covered by the bottom portion 34 of the hollow plunging tube 28, thus preventing the flow of liquids between the hollow syringe barrel cavity 44 and the hollow plunging tube cavity 42.

Now referring to FIGS. 8-11, a second embodiment is illustrated. The second embodiment is provided with a hollow syringe barrel 18 (analogous to that shown in FIGS. 5-6) to contain the unseparated solution or separated layer (s), as applicable given the stage of processing and isolation of the liquid. As in the first embodiment, a perforated plunger seal 20 which has an outer perimeter 22 that resides flush against an interior surface 24 of the hollow syringe barrel 18 is provided with an at least one seal hole 26. In a preferred embodiment, 2 to 4 seal holes are used, but 1 to more than 4 seal holes may be used. A hollow plunging tube 28 is provided with a sealed bottom 54. The hollow plunging tube 28 is threadably coupled to the perforated plunger seal 20 via an at least one male interlocking thread 40 adjacent to the sealed bottom 54. The at least one female interlocking thread 38 on the perforated plunger seal 20 is aligned to correspond with at least one male interlocking thread 40 located on the bottom portion 34 of the hollow plunging tube 28. The hollow plunging tube 28 is optionally provided with at least one relief hole 30 located in an upper portion of the hollow plunging tube 28 as illustrated in FIG. 19, where the upper portion includes the top quarter of the hollow plunging tube 28 and includes both a wall 36 of the hollow plunging tube 28 and the top portion 32. The sealed bottom 54 of the hollow plunging tube 28 is provided with an at least one tube hole 56. In a preferred embodiment, 2 to 4 tube holes are used but 1 to more than 4 tube holes may be used. In operation, a beveled needle hub 46 on the lower end 48 of the hollow syringe barrel 18 allows liquids to be pushed out of the hollow syringe barrel cavity 44.

The second embodiment allows for the hollow plunging tube 28 to be rotated with respect to the perforated plunger seal 20 to set said hollow plunging tube 28 to the open position 50; this operation is analogous to that shown in FIG. 5 for the first embodiment. The hollow plunging tube 28 set to the open position 50 creates a seal cavity 58 within the perforated plunger seal 20. In the open position, the at least one seal hole 26 permits liquids to flow from the hollow syringe barrel cavity 44, through the seal cavity 58, through the one or more tube holes 56, and into the hollow plunging tube cavity 42.

Now referring to FIG. 10, the hollow plunging tube 28 is rotated with respect to the perforated plunger seal 20 to set the hollow plunging tube 28 to the closed position. The seal cavity 58 is thus collapsed while the at least one seal hole 26 and the at least one tube hole 56 are misaligned, preventing the flow of liquids between the hollow syringe barrel cavity 44 and the hollow plunging tube cavity 42.

Now referring to FIGS. 12-17, a third embodiment is illustrated. The third embodiment is provided with a hollow syringe barrel 18 to contain the liquid. As in the previous embodiments, a perforated plunger seal 20 is provided that has an outer perimeter 22 which resides flush against an interior surface 24 of the hollow syringe barrel 18 and is provided with an at least one seal hole 26. In a preferred embodiment, 2 to 4 seal holes are used, but 1 to more than 4 seal holes may be used. A hollow plunging tube 28 is provided with a sealed bottom 54 with an at least one tube hole 56. The at least one tube hole 56 resides in operational relationship to the at least one seal hole 26. In a preferred embodiment, 2 to 4 tube holes are used but 1 to more than 4 tube holes may be used. It is preferred that the bottom portion 34 of the hollow plunging tube 28 is a conical trapezoidal shape 60 that fits flushly within the perforated plunger seal 20 when in an open or a closed position; however, it is understood that other shapes may be used, for instance, to accommodate alternative shapes of a perforated plunger seal 20.

The hollow plunging tube 28 is coupled flushly by a lip 62 on the conical trapezoidal shape 60 of the hollow plunging tube 28 when inserted into an interior groove 64 of the trapezoidal shape perforated plunger seal 20. A beveled needle hub 46 on the lower end 48 of the hollow syringe barrel 18 allows liquids to be pushed out of the hollow syringe barrel cavity 44. An optional relief hole 30 is located on the top portion 32 of the hollow plunging tube 28. Alternatively, the at least one relief hole 30 may be located on the side of the hollow plunging tube 28; in such embodiments, the at least one relief hole 30 will preferably be located within the upper half of the hollow plunging tube 28 and more preferably will be located within the upper quarter of the hollow plunging tube 28. An optional feature of this embodiment is a removable stop cap 66 that is used to seal the relief hole 30 and enable creation of a vacuum within the hollow plunging tube 28.

Figure 17:
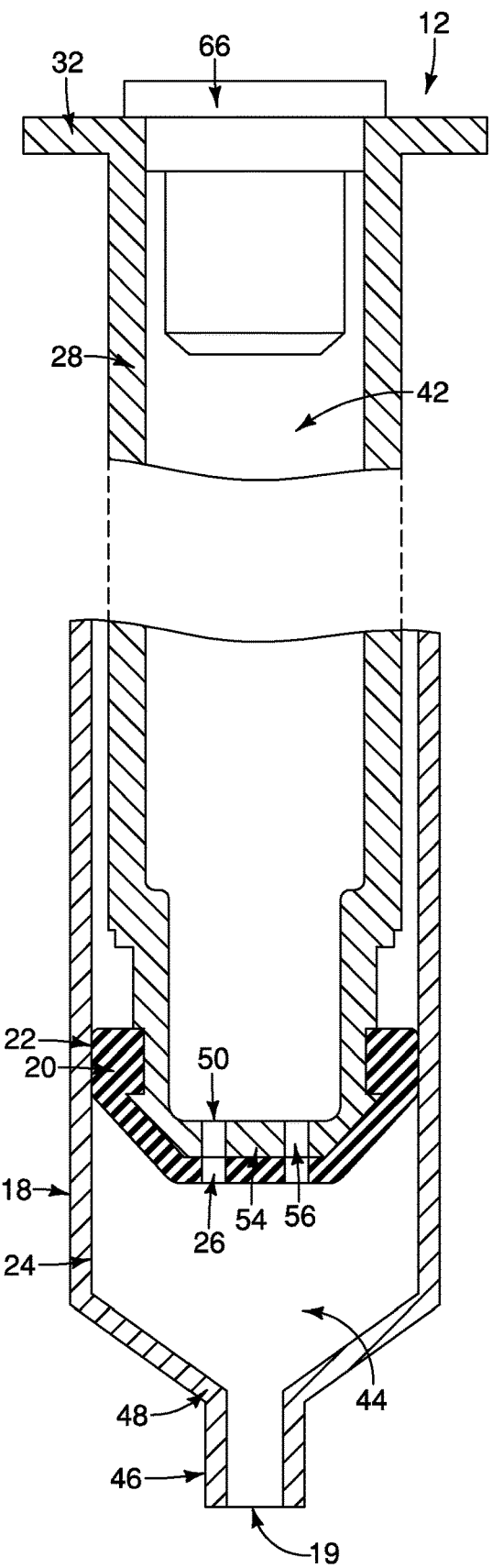
FIG. 17 illustrates a cross-sectional view of the hollow syringe barrel, the hollow plunging tube, and the corresponding perforated plunger seal in the open position for the third embodiment.
Figure 22:
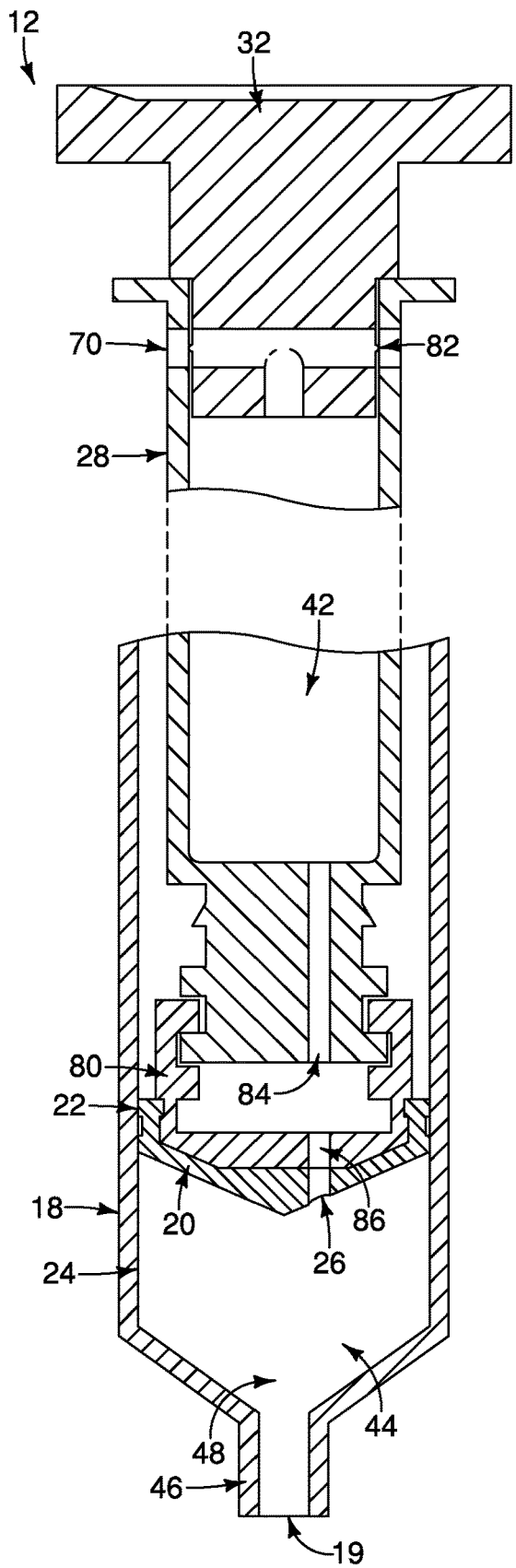
FIG. 22 illustrates a cross-sectional view of the removable stop cap, the hollow plunging tube, the bottom portion adapter, the corresponding perforated plunger seal, and the hollow syringe barrel set to the open position in the fourth embodiment.

Now referring to FIGS. 14 and 17, the hollow plunging tube 28 is rotated to the open position 50 so that at least one tube hole 56 and the at least one seal hole 26 align. The open position 50 allows the adjacent liquids to pass between the hollow syringe barrel cavity 44 and the hollow plunging tube cavity 42.

Figure 16:
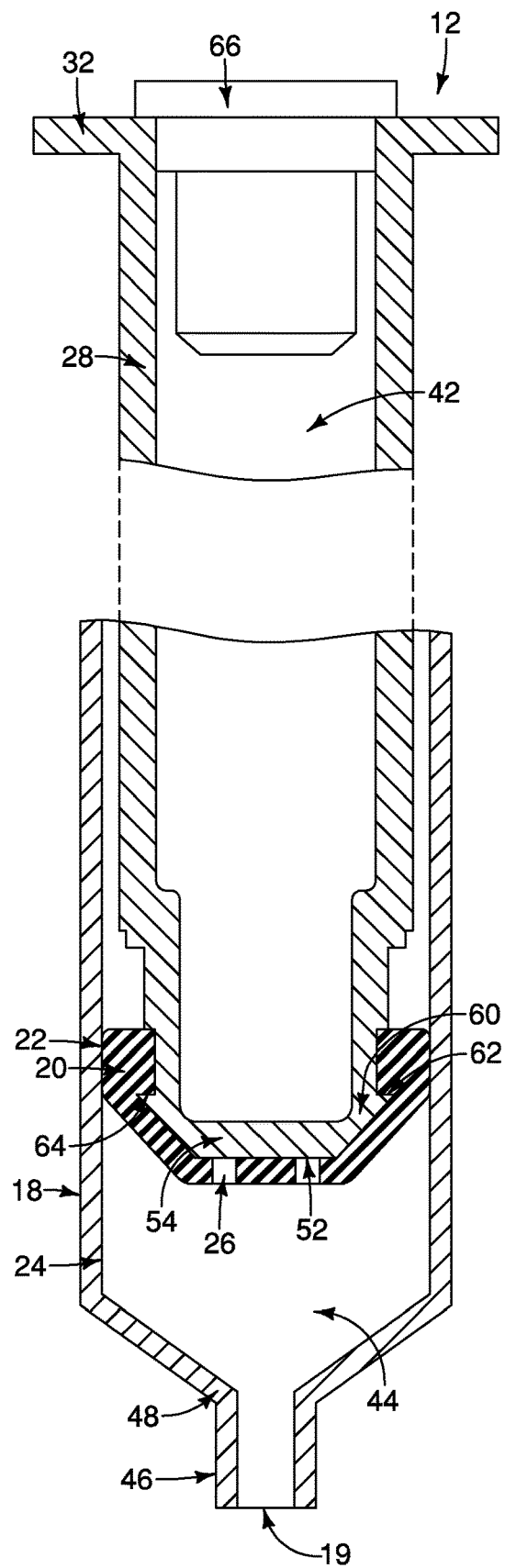
FIG. 16 illustrates a cross-sectional view of a hollow syringe barrel, the hollow plunging tube, and the corresponding perforated plunger seal in the closed position for the third embodiment.

Now referring to FIG. 16, the hollow plunging tube 28 is rotated to a closed position 52 so that at least one tube hole 56 and the corresponding at least one seal hole 26 are misaligned. The closed position 52 prevents adjacent liquids from passing between the hollow syringe barrel cavity 44 and the hollow plunging tube cavity 42.

Now referring to FIGS. 18-23, a fourth embodiment is illustrated. The fourth embodiment is provided with a hollow syringe barrel 18 to contain the liquid. As in the previous embodiments, a perforated plunger seal 20 is provided that has an outer perimeter 22, which resides flush against an interior surface 24 of the hollow syringe barrel 18 and is provided with an at least one seal hole 26. In a preferred embodiment, 2 to 4 seal holes are used, but 1 to more than 4 seal holes may be used. The bottom portion adapter 80 resides in operational proximity to said perforated plunger seal 20. The perforated plunger seal 20 is attached to a bottom portion adapter 80 such that the seal hole 26 aligns with the bottom portion adapter hole 86. As in the third embodiment, a lip 62 is optionally provided and is located on the bottom portion adapter 80; this lip 62 corresponds to an interior grove 64 located on the interior of the perforated plunger seal 20. In the preferred embodiment, the bottom portion adapter 80 resides flush against the perforated plunger seal 20 to create a continuous piece; however, it is noted that the bottom portion adapter 80 may optionally reside partially flush against the perforated plunger seal 20 to achieve a similar effect of a continuous piece. The bottom portion adapter 80 threadably corresponds to the hollow plunging tube 28 which features a sealed bottom 54 perforated by an at least one tube hole 56.

Figure 23:
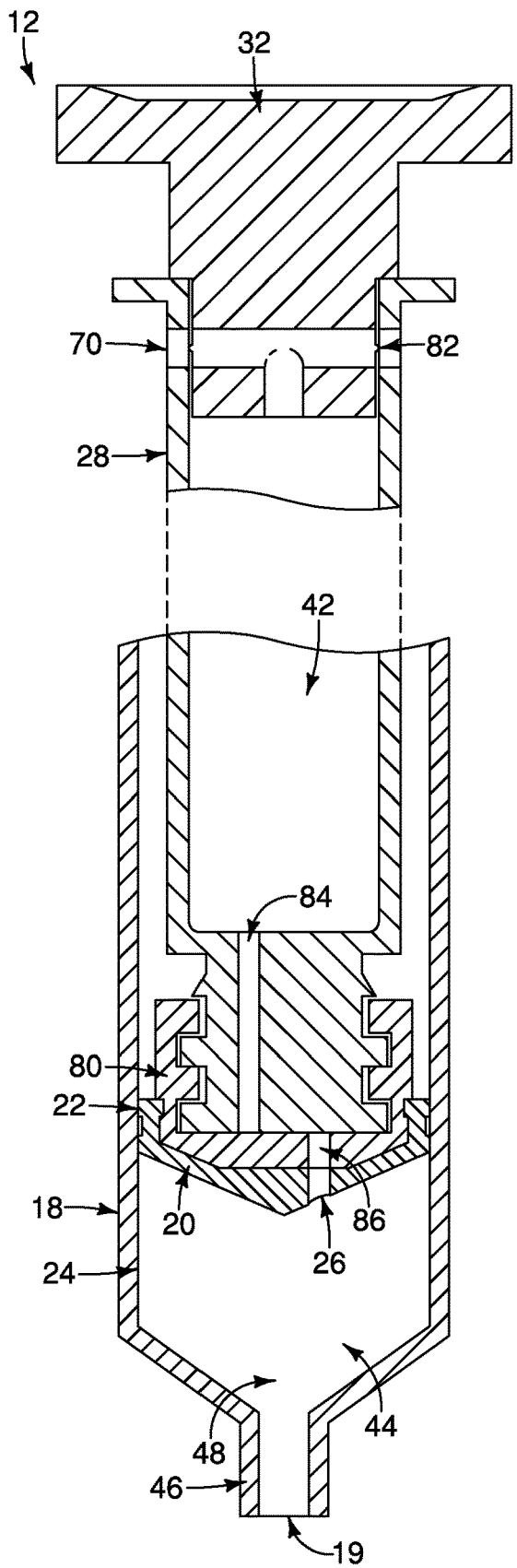
FIG. 23 illustrates a cross-sectional view of the removable stop cap, the hollow plunging tube, the bottom portion adapter, the corresponding perforated plunger seal, and the hollow syringe barrel set to the closed position in the fourth embodiment.

The bottom portion adapter hole 86 is positioned below the tube hole 56 by rotating the hollow plunging tube 28 to the open position. This rotation is realized by rotating the hollow plunging tube 28 with respect to the syringe tube, where friction between the perforated plunger seal 20 and the interior surface 24 hold the perforated plunger seal 20 and the bottom adapter portion 80 stationary with respect to the hollow syringe barrel 18. In the open position of this embodiment, sufficient space is created to form a passage cavity that allows fluids to flow from the hollow syringe barrel cavity 44 to the hollow plunging tube cavity 42. When the hollow plunging tube 28 is rotated in a direction to advance the sealed bottom 54 into the bottom portion adaptor 80, the sealed bottom 54 will stop advancing when the sealed bottom 54 resides flush with a lower end of the bottom portion adaptor 80. This position is referred to as the closed position where liquids are prevented from flowing between the hollow syringe barrel cavity 44 of the hollow syringe barrel 18 and the hollow plunging tube cavity 42 of the hollow plunging tube 28. At this closed position, the bottom portion adapter hole 86 is not aligned with the tube hole 56. This closed position is illustrated in FIG. 20 and FIG. 23.

Now referring to FIGS. 18-23, a fourth embodiment is illustrated. The fourth embodiment is provided with a hollow syringe barrel 18 to contain the liquid. As in the previous embodiments, a perforated plunger seal 20 is provided that has an outer perimeter 22, which resides flush against an interior surface 24 of the hollow syringe barrel 18 and is provided with an at least one seal hole 26. In a preferred embodiment, 2 to 4 seal holes are used, but 1 to more than 4 seal holes may be used. The bottom portion adapter 80 resides in operational proximity to said perforated plunger seal 20. The perforated plunger seal 20 is attached to a bottom portion adapter 80 such that the seal hole 26 aligns with the bottom portion adapter hole 86. As in the third embodiment, a lip 62 is optionally provided and is located on the bottom portion adapter 80; this lip 62 corresponds to an interior grove 64 located on the interior of the perforated plunger seal 20. In the preferred embodiment, the bottom portion adapter 80 resides flush against the perforated plunger seal 20 to create a continuous piece; however, it is noted that the bottom portion adapter 80 may optionally reside partially flush against the perforated plunger seal 20 to achieve a similar effect of a continuous piece. The bottom portion adapter 80 threadably corresponds to the hollow plunging tube 28 which features a sealed bottom 54 perforated by an at least one tube hole 56.

The bottom portion adapter hole 86 is positioned below the tube hole 56 by rotating the hollow plunging tube 28 to the open position. This rotation is realized by rotating the hollow plunging tube 28 with respect to the syringe tube, where friction between the perforated plunger seal 20 and the interior surface 24 hold the perforated plunger seal 20 and the bottom adapter portion 80 stationary with respect to the hollow syringe barrel 18. In the open position of this embodiment, sufficient space is created to form a passage cavity that allows fluids to flow from the hollow syringe barrel cavity 44 to the hollow plunging tube cavity 42. When the hollow plunging tube 28 is rotated in a direction to advance the sealed bottom 54 into the bottom portion adaptor 80, the sealed bottom 54 will stop advancing when the sealed bottom 54 resides flush with a lower end of the bottom portion adaptor 80. This position is referred to as the closed position where liquids are prevented from flowing between the hollow syringe barrel cavity 44 of the hollow syringe barrel 18 and the hollow plunging tube cavity 42 of the hollow plunging tube 28. At this closed position, the bottom portion adapter hole 86 is not aligned with the tube hole 56. This closed position is illustrated in FIG. 20 and FIG. 23.

In a preferred embodiment, a removable stop cap 66 is insertable into the top portion 32; the removable stop cap 66 is optionally provided with a ridged edging 72. The ridged edging 72 comprises of indentations to accommodate simple gripping, but the ridged edging may also comprise of other known gripping edging as are well known in the art. Also, the hollow plunging tube 28 may optionally be provided with ridges 68 as well. In a preferred embodiment, the hollow plunging tube 28 is provided with an at least one ridge 68. Most preferably, 2-4 ridges 68 are provided, but there may be more than 4, which increases the stability of the hollow plunging tube 28 within the hollow syringe barrel 18. The bottom portion adapter 80 has an option for bottom portion adapter ridges 90. The purpose for the ridged edging 72, the additional ridges 68, and the bottom portion adapter ridges 90 is to maintain stability, create a firm grip between the user and the device itself, and to reduce the amount of material necessary to create each element.

The removable stop cap 66 is insertable into the hollow plunging tube 28. The removable stop cap has a side relief hole ridge 76 that coincides with a hollow plunging tube notch 82 located in the hollow plunging tube 28. The side relief hole ridge 76 stabilizes the removable stop cap 66 when placed inside the hollow plunging tube 28. Then the removable stop cap rotates to a relief position wherein the at least one top portion relief hole 78 aligns with an at least one side relief hole 70 located on the hollow plunging tube 28, thereby creating a means to allow fluids to escape from within a hollow plunging tube cavity 42 of said hollow plunging tube 28. Conversely, the removable stop cap 66 is rotatable to a sealed position wherein the at least one top portion relief hole on the top portion misaligns with the at least one side relief hole located on the hollow plunging tube creating a seal within the hollow plunging tube cavity of the hollow plunging tube to prevent fluids from escaping. Alternatively to the specific side relief hole described above, the fourth embodiment may include at least one relief hole 30 located in an upper portion of the hollow plunging tube 28 as illustrated in FIG. 19, where the upper portion includes the top quarter of the hollow plunging tube 28 and includes both a wall 36 of the hollow plunging tube 28 and the removable stop cap 66.

Now referring to illustrations C and D in FIG. 7, operations of the above described embodiments are substantially similar. After the liquids have been separated, the light density liquid is extracted into the hollow plunging tube 28 as force is exerted in a downward motion on the hollow plunging tube 28 resulting in a position change of the hollow plunging tube 28 within the hollow syringe barrel 18. Once the hollow plunging tube 28 has captured substantially all of the light density liquid, the hollow plunging tube is moved from an open position 50 to a closed position 52. In the presently described embodiments, the movement from an open position 50 to a closed position 52 is created by rotating the hollow plunging tube 28 in relation to the male interlocking thread 40. A hub cap 74 can then be removed to allow the heavy density liquid to be removed from the discharge opening 19 as shown in illustrations E and F in FIG. 7. Once the hub cap 74 is removed, the hollow plunging tube 28 may be advanced further in a downward direction into the hollow syringe barrel 18 until substantially all or all of the heavy density liquid is removed. Once this operation is complete, the hub cap 74 may be reinserted to preserve the middle density liquid, in the case of the exemplary application discussed herein, until ready for use. When the syringe device 12 is ready for operation, a needle or other delivery piece may be employed on the beveled needle hub 46 to deploy the middle density liquid.

Now referring to FIGS. 24-32, a fifth embodiment is illustrated. The fifth embodiment is provided with a hollow syringe barrel 18 to contain the liquid. As in the previous embodiments, a perforated plunger seal 20 is provided that has an inner perimeter 21 and an outer perimeter 22, which resides flush against an interior surface 24 of the hollow syringe barrel 18 and where the perforated plunger seal is provided with an at least one seal hole 26. In a preferred embodiment, 1 seal hole is used, but more than 1 seal holes may be used if desired. A bottom portion adapter 80 resides in operational proximity to the perforated plunger seal 20. The perforated plunger seal 20 is attached to a bottom portion adapter 80 such that the seal hole 26 aligns with an at least one bottom portion adapter hole 86. In the preferred embodiment, the bottom portion adapter 80 resides flush against an outer surface 83 of the inner perimeter 21 of the perforated plunger seal 20 to create a continuous piece; however, it is noted that the bottom portion adapter 80 may optionally reside partially flush against an outer surface 83 of the inner perimeter 21 of the perforated plunger seal 20 to achieve a similar effect of a continuous piece. Furthermore, in the preferred embodiment, a plurality of bottom portion adapter holes 86 are provided, but one bottom portion adapter hole is needed that corresponds with the seal hole 26.

A hollow plunging tube 28 is provided and is in operational relationship with the bottom portion adapter 80. The hollow plunging tube 28 is provided with a bottom portion 34 containing a bottom portion opening 35. The bottom portion opening 35 is positioned away from the at least one bottom portion adapter hole 86 by rotating the bottom portion adapter 80 to the open position. This rotation is realized by rotating the hollow plunging tube 28 with respect to the bottom portion adapter 80, where friction between the perforated plunger seal 20 and the bottom portion adapter 80 hold the perforated plunger seal 20 and the bottom adapter portion adapter 80 stationary with respect to the hollow syringe barrel 18. In the open position of this embodiment, sufficient space is created to form a passage cavity that allows fluids to flow from the hollow syringe barrel cavity 44 to the hollow plunging tube cavity 42. When the hollow plunging tube 28 is rotated in a direction toward the at least one bottom portion adapter hole 86, the bottom portion 34 of the hollow plunging tube 18 will stop advancing when the bottom portion 54 resides flush with a lower end of the bottom portion adaptor 80. This position is referred to as the closed position where liquids are prevented from flowing between the hollow syringe barrel cavity 44 of the hollow syringe barrel 18 and the hollow plunging tube cavity 42 of the hollow plunging tube 28.

Figure 24:
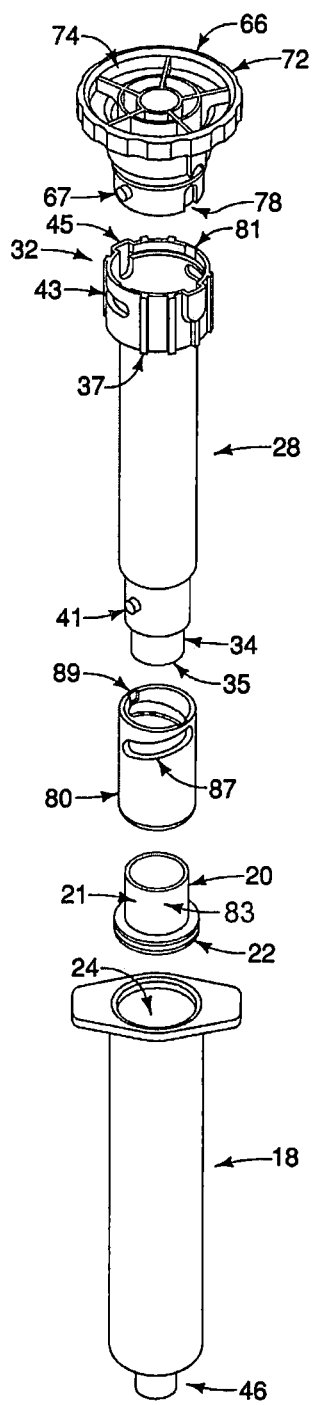
FIG. 24 illustrates a top-down, side perspective of the removable stop cap, the hollow plunging tube, the bottom portion adapter, the corresponding perforated plunger seal and hollow syringe barrel in a fifth embodiment.
Figure 25:
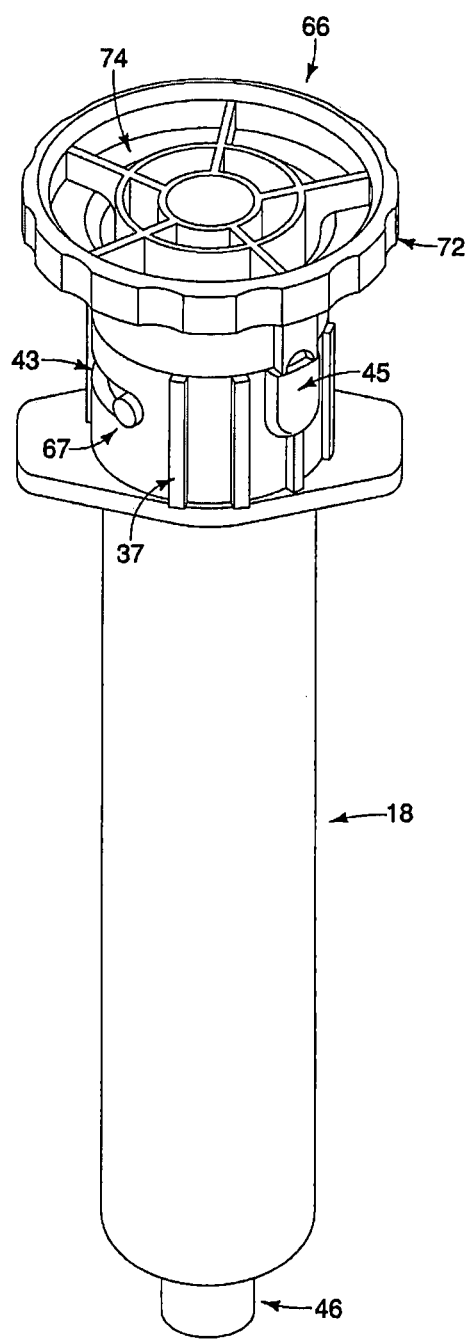
FIG. 25 illustrates a top-down, side perspective of the removable stop cap and the corresponding top portion relief hold in a closed position in the fifth embodiment.

Referring to FIGS. 24 and 25, the bottom portion adapter 80 is optionally provided with an at least one bottom portion adapter guide rail 87 where the hollow plunging tube 28 will include at least one hollow plunging tube guide peg 41 that corresponds to the at least one bottom portion guide rail 87. The bottom portion adapter 80 may further include an at least one bottom portion adapter access groove 89 through which the at least one hollow plunging tube guide peg 41 is provided a means to access the at least one bottom portion adapter guide rail 87.

Another feature of this embodiment is a removable stop cap 66 in operational relationship with a top portion 32 of the hollow plunging tube 28. The removable stop cap 66 is provided with an at least one top portion relief hole 78 used to seal a hollow plunging tube side relief slot 45 when twisted and moved to misalign with hollow plunging tube side relief slot 45. This position enables the creation of a vacuum within the hollow plunging tube 28 and prevents air from escaping. The removable stop cap 66 is optionally provided with an at least one removable stop cap guide peg 67 which resides within a hollow plunging tube guide rail 43 when in operation. The removable stop cap 66 may further include an at least one hollow plunging tube access groove 81 through which the at least one removable stop gap guide peg 67 is provided a means to access the at least one bottom portion adapter guide rail 43.

Optionally, the removable stop cap 66 may be rotatable to a sealed position wherein the at least one hollow plunging tube side relief slot 45 on the hollow plunging tube 28 misaligns with an at least one top portion relief hole 78 located on the removable stop cap 66 creating a seal within the hollow plunging tube cavity 42 of the hollow plunging tube 28 to prevent fluids from escaping. When the at least one hollow plunging tube side relief slot 45 aligns with the at least one top portion relief hole 78, the removable stop cap 66 is in the unsealed position as illustrated in FIG. 25 allowing fluids to escape.

Figure 30:
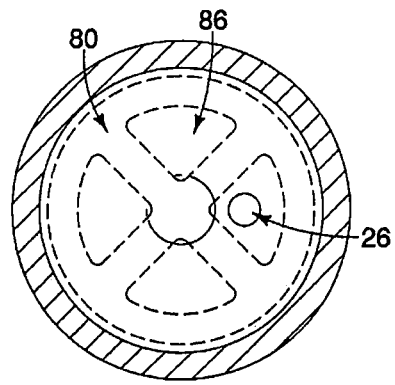
FIG. 30 illustrates a planar view from a bottom perspective of the perforated plunger seal and the bottom portion adapter in the fifth embodiment.
Figure 31:
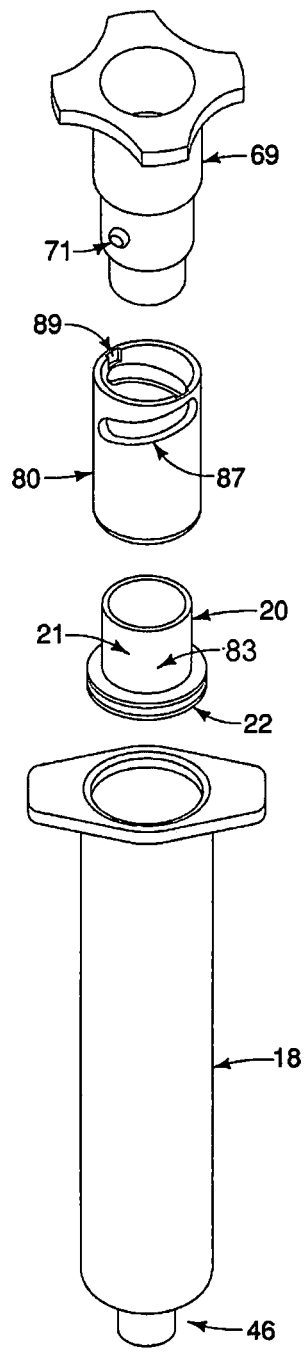
FIG. 31 illustrates a top-down, exploded view of the temporary stop cap, the hollow plunging tube and the corresponding bottom portion adapter and the perforated plunger seal in the fifth embodiment.
Figure 32:
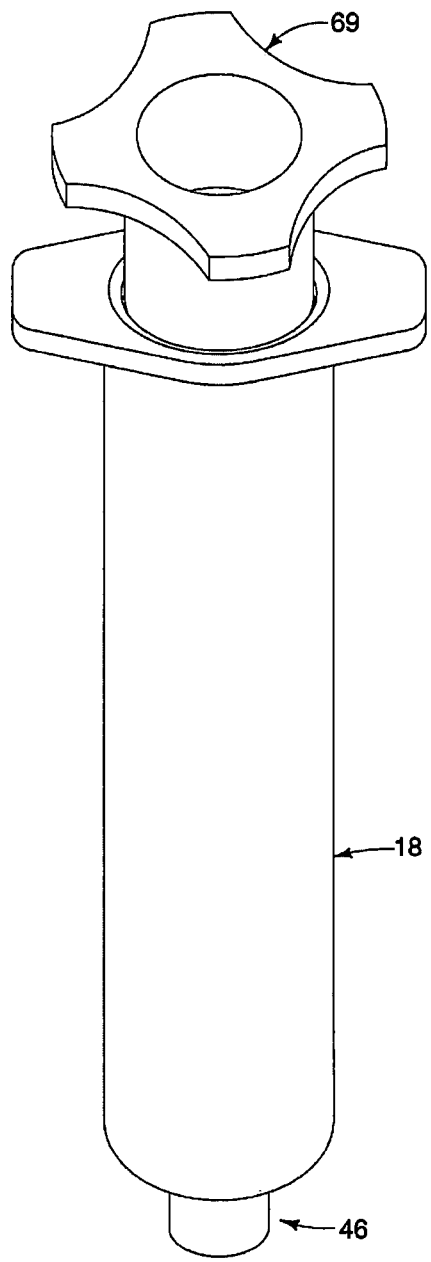
FIG. 32 illustrates a top-down, side perspective view of the temporary stop cap, bottom portion adapter and the corresponding perforated plunger seal in the fifth embodiment.

Now referring to FIGS. 24, 26, 28, 29 and 30, the bottom portion adapter 80 may optionally be rotatable to a closed position from an opened position. The opened position is established when the at least one bottom portion adapter hole 86 located on the bottom portion adapter 80 moves away from the bottom portion opening 35 on the hollow plunging tube 28 creating a cavity within the bottom portion adapter 80 allowing fluids. Fluids are allowed to enter through the at least one bottom portion adapter hole 86 of the bottom portion adapter 80 from the hollow syringe barrel 18. This action is enabled because the at least one bottom portion adapter hole 86 aligns with the at least one seal hole 26 located on the perforated plunger seal 20 as illustrated in FIG. 30.

Figure 26:
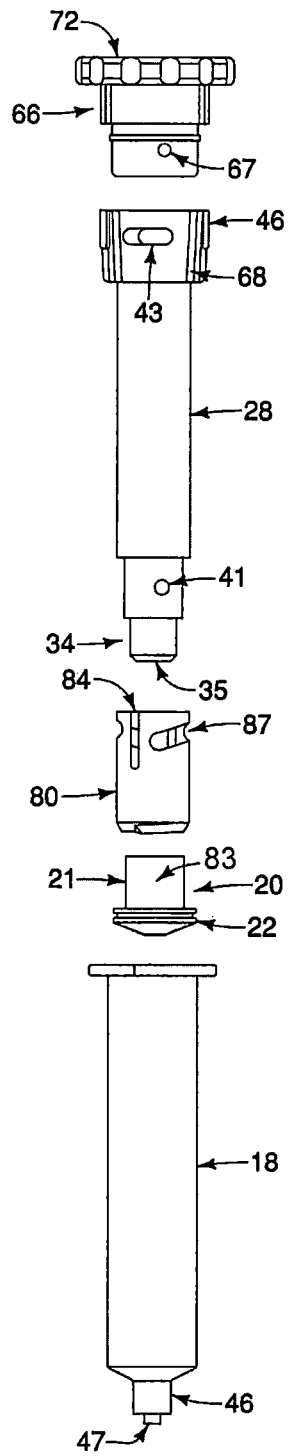
FIG. 26 illustrates a side perspective of the removable stop cap, the hollow plunging tube, the bottom portion adapter, the corresponding perforated plunger seal and the hollow syringe barrel in the fifth embodiment.
Figure 27:
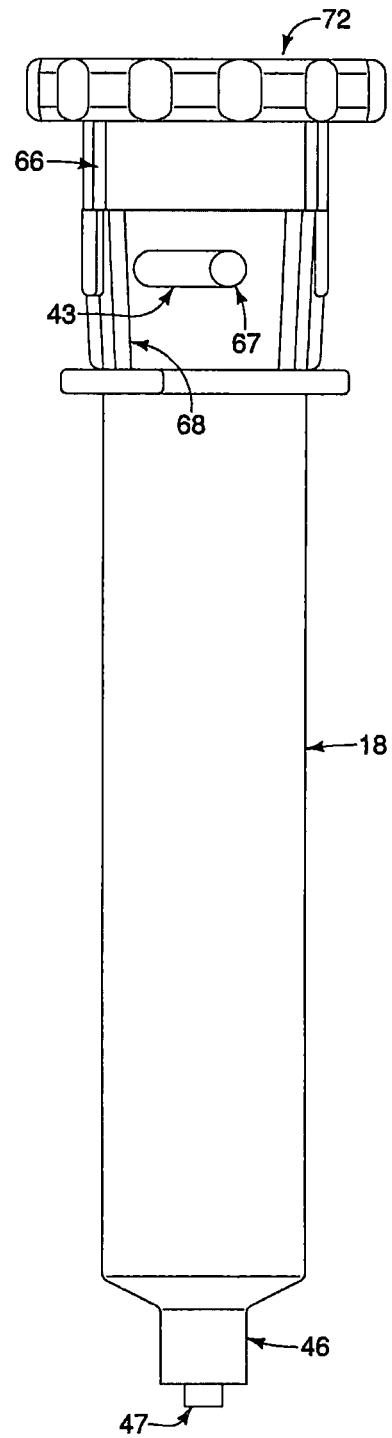
FIG. 27 illustrates a side perspective of the removable stop cap and the corresponding top portion relief hold in a closed position in the fifth embodiment.
Figure 28:
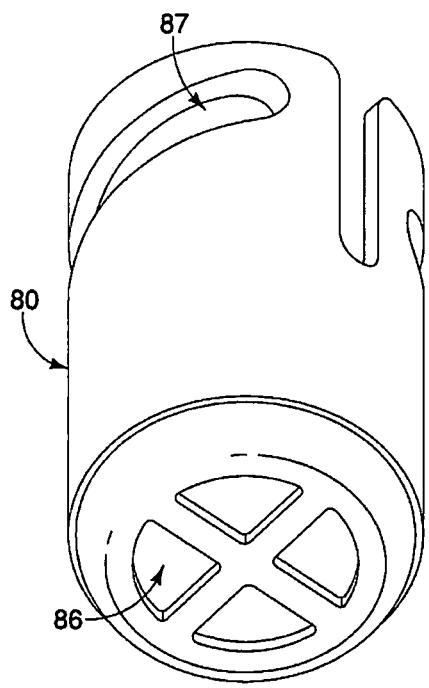
FIG. 28 illustrates a bottom-up, side perspective view of the bottom portion adapter and the corresponding bottom portion adapter guide rail and bottom portion adapter holes in the fifth embodiment.
Figure 29:
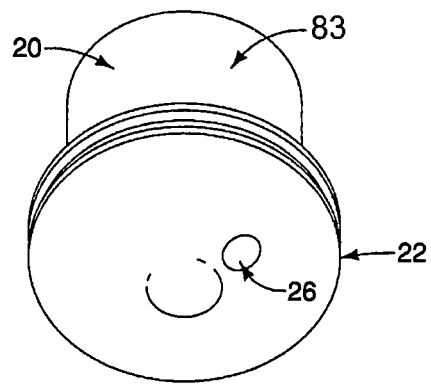
FIG. 29 illustrates a bottom-up, side perspective view of the perforated plunger seal and the corresponding seal hole in the fifth embodiment.

Now referring to FIGS. 26 and 27, the fifth embodiment of the syringe device 12 is optionally provided with a beveled needle hub 46 in operational relationship with the hollow syringe barrel 18. The syringe device 12 optionally includes a needle stop cap 47 in operational relationship with the beveled needle hub 46.

Now referring to FIGS. 28, 29, 31 and 32, the fifth embodiment of the syringe device 12 is optionally provided with a temporary stop cap 69 in operational relationship with the bottom portion adapter 80. The purpose of the temporary stop cap 69 is to provide lower clearance so that the hollow syringe barrel 18 fits inside a centrifuge or similar device where such clearance would not otherwise be available through the use of the hollow plunging tube 28 and the removable stop cap 66. The temporary stop cap 69 is optionally provided with an at least one temporary stop cap guide peg 71 that may be fed onto the bottom portion adapter 80 via an at least one bottom portion adapter access groove 89. The operations of the temporary stop cap guide peg 71 work similarly to the hollow plunging tube guide peg 41, where the temporary stop cap 69 is moveable from an open position to a closed position in a similar manner as the hollow plunging tube 28 did when it was in operational relationship with the bottom portion adapter 80.

Also provided herein is a method of separating a light density fluid, a middle density fluid and a heavy density fluid from a sample containing a mixture of the light density fluid, the middle density fluid and the heavy density fluid within the syringe device 12. The method involves several steps. The first step includes extracting the sample from a subject by pulling a hollow plunging tube 28 in a reverse manner until a hollow syringe barrel 18 is filled with the sample. A next step includes placing a needle stop cap 47 on a beveled needle hub 46 on the hollow syringe barrel 18. A next step includes using a separating force such that substantially all (an amount of volume equaling ninety percent (90%) or more of the original volume of the heavy density fluid) of the heavy density fluid is forced to a bottom of the hollow syringe barrel 18. A next step includes rotating a removable stop cap 66 until an at least one top portion relief hole 78 on the removable stop cap 66 is in an unsealed position. Another step includes rotating the hollow plunging tube 28 until a bottom portion adapter 80 in operational relationship with a perforated plunger seal 20 and the hollow plunging tube 28 is in an open position. A next step includes filling the hollow plunging tube 18 with substantially all (an amount of volume equaling ninety percent (90%) or more of the original volume of the light density fluid) of the light density fluid by pushing the hollow plunging tube 28 in a forward manner. A next step includes rotating the hollow syringe barrel 18 until the bottom portion adapter 80 is in a closed position. An optional next step includes removing the needle stop cap 47 from the beveled needle hub 46 and optionally pushing the hollow plunging tube 18 in a forward manner.

Optionally, for the method described in the paragraph above, the hollow plunging tube 28 may be pushed forward until substantially all (an amount of volume equaling ninety percent (90%) or more of the original volume of the heavy density fluid) of the heavy density fluid is removed from the hollow syringe barrel 18. In addition, the separating force used may also be gravity or centrifugal force.

Alternatively, another method is provided herein for separating a light density fluid, a middle density fluid and a heavy density fluid from a sample containing a mixture of the light density fluid, the middle density fluid and the heavy density fluid within a syringe device. The method involves several steps. A first step includes extracting a sample from a subject by pulling a hollow plunging tube 28 in a reverse manner until a hollow syringe barrel 18 is filled with the sample. A next step includes placing a needle stop cap 47 on a beveled needle hub 46 on said hollow syringe barrel 18. A next step includes removing said hollow plunging tube 28 from a bottom portion adapter 80 in operational relationship with a perforated plunger seal 20 and the hollow plunging tube 28. A next step includes placing a temporary stop cap 69 on the bottom portion adapter 80 via an at least one temporary stop cap guide peg 71. A next step includes using a separating force such that substantially all (an amount of volume equaling ninety percent (90%) or more of the original volume of the heavy density fluid) of the heavy density fluid is forced to a bottom of the hollow syringe barrel 18. A next step includes removing the temporary stop cap 69 from the bottom portion adapter 80 and placing the hollow plunging tube 28 on the bottom portion adapter 80 such that the hollow plunging tube 28 is in operational relationship with the bottom portion adapter 80. A next step includes rotating the removable stop cap 66 on said hollow plunging tube 28 until an at least one top portion relief hole 78 on the removable stop cap 66 is in an unsealed position. Another step includes rotating the hollow plunging tube 28 until a bottom portion adapter 80 in operational relationship with a perforated plunger seal 20 is in an open position. A next step includes filling the hollow plunging tube 28 with substantially all (an amount of volume equaling ninety percent (90%) or more of the original volume of the light density fluid) of the light density fluid by pushing the hollow plunging tube 28 in a forward manner. A next step includes rotating the hollow syringe barrel 18 until the bottom portion adapter 80 is in a closed position. An optional next step includes removing the needle stop cap 47 from said beveled needle hub 46 and pushing the hollow plunging tube 28 in a forward manner.

Optionally, for the method described in the paragraph above, the hollow plunging tube 28 may be pushed forward until substantially all (an amount of volume equaling ninety percent (90%) or more of the original volume of the heavy density fluid) of the heavy density fluid is removed from the hollow syringe barrel 18. In addition, the separating force used may also be gravity or centrifugal force.

While several particular embodiments of the present invention have been described herein, it will be appreciated by those skilled in the art that changes and modifications may be made thereto without departing from the invention in its broader aspects and as set forth in the following claims.

We claim:

1. A syringe device for separating liquids of different densities comprising of:
   a hollow syringe barrel;
   a perforated plunger seal with an inner perimeter and an outer perimeter, wherein said outer perimeter resides flush against an interior surface of said hollow syringe barrel and wherein said perforated plunger seal is provided with an at least one seal hole;
   a bottom portion adapter in operational relationship with said perforated plunger seal, wherein said bottom portion adapter resides flush against an outer surface of said inner perimeter of said perforated plunger seal and includes an at least one bottom portion adapter hole which aligns with said at least one seal hole located on said perforated plunger seal;
   a hollow plunging tube in operational relationship with said bottom portion adapter, wherein said hollow plunging tube is provided with a bottom portion containing a bottom portion opening, wherein said bottom portion is rotatable from an open position and a closed position; and
   a removable stop cap in operational relationship with a top portion of said hollow plunging tube, wherein said removable stop cap is provided with an at least one top portion relief hole.

2. The syringe device of claim 1 wherein said bottom portion adapter includes an at least one bottom portion adapter guide rail and wherein said hollow plunging tube includes an at least one hollow plunging tube guide peg that corresponds to said at least one bottom portion adapter guide rail.

3. The syringe device of claim 2 wherein said bottom portion adapter further includes an at least one bottom portion adapter access groove through which said at least one hollow plunging tube guide peg is provided a means to access said at least one bottom portion adapter guide rail.

4. The syringe device of claim 1 wherein said removable stop cap further includes an at least one removable stop cap guide peg which resides within a hollow plunging tube guide rail through access granted from a hollow plunging tube access groove.

5. The syringe device of claim 4 wherein said removable stop cap further includes an at least one hollow plunging tube access groove through which said at least one removable stop cap guide peg is provided a means to access said an at least one hollow plunging tube guide rail.

6. The syringe device of claim 1 wherein said removable stop cap is rotatable to a sealed position, wherein at said sealed position said at least one top portion relief hole on said removable stop cap misaligns with an at least one hollow plunging tube side relief slot located on said hollow plunging tube.

7. The syringe device of claim 1, wherein said bottom portion adapter is rotatable to a closed position, wherein said opened position is established when said at least one bottom portion adapter hole located on said bottom portion adapter moves away from said bottom portion opening on said hollow plunging tube.

8. The syringe device of claim 1, wherein a beveled needle hub is in operational relationship with said hollow syringe barrel.

9. The syringe device of claim 8, wherein a needle stop cap is in operational relationship with said beveled needle hub.

10. The syringe device of claim 1, wherein a temporary stop cap is in operational relationship with said bottom portion adapter.

11. A method of separating a light density fluid, a middle density fluid and a heavy density fluid from a sample containing a mixture of the light density fluid, the middle density fluid and the heavy density fluid within a syringe device, said method comprises the steps:
    extracting the sample from a subject by pulling a hollow plunging tube in a reverse manner until a hollow syringe barrel is filled with the sample,
    placing a needle stop cap at a beveled needle hub on said hollow syringe barrel;
    using a separating force such that substantially all of heavy density fluid is forced to a bottom of said hollow syringe barrel;
    rotating a removable stop cap until an at least one top portion relief hole on said removable stop cap is in an unsealed position and rotating said hollow plunging tube until a bottom portion adapter in operational relationship with a perforated plunger seal and said hollow plunging tube is in an open position;
    filling said hollow plunging tube with substantially all of the light density fluid by pushing said hollow plunging tube in a forward manner; and
    rotating said hollow syringe barrel until said bottom portion adapter is in a closed position.

12. The method off claim 11 wherein said hollow plunging tube is pushed forward until substantially all of the heavy density fluid is removed from said hollow syringe barrel.

13. The method of claim 11 wherein the separating force is gravity.

14. The method of claim 11 wherein the separating force is centrifugal.

15. The method of claim 11, further comprising the steps: removing said needle stop cap from said beveled needle hub.

16. The method of claim 11, further comprising the steps: pushing said hollow plunging tube in a forward manner.

17. A method of separating a light density fluid, a middle density fluid and a heavy density fluid from a sample containing a mixture of the light density fluid, the middle density fluid and the heavy density fluid within a syringe device, said method comprises the steps:

extracting the sample from a subject by pulling a hollow plunging tube in a reverse manner until a hollow syringe barrel is filled with the sample, placing a needle stop cap at a beveled needle hub on said hollow syringe barrel;

removing said hollow plunging tube from a bottom portion adapter in operational relationship with a perforated plunger seal and said hollow plunging tube;

placing a temporary stop cap in operational relationship with said bottom portion adapter;

using a separating force such that substantially all of the heavy density fluid is forced to a bottom of said hollow syringe barrel;

removing said temporary stop cap;

placing said hollow plunging tube in operational relationship with said bottom portion adapter and said removable stop cap;

rotating said removable stop cap until an at least one top portion relief hole on said removable stop cap is in an unsealed position and rotating said hollow plunging tube until a bottom portion adapter in operational relationship with a perforated plunger seal and said hollow plunging tube is in an open position;

filling said hollow plunging tube with substantially all of the light density fluid by pushing said hollow plunging tube in a forward manner; and rotating said hollow syringe barrel until said bottom portion adapter is in a closed position.

18. The method off claim 17 wherein said hollow plunging tube is pushed forward until substantially all of the heavy density fluid is removed from said hollow syringe barrel.

19. The method of claim 17 wherein the separating force is centrifugal.

20. The method of claim 17, further comprising the steps:
removing said needle stop cap from said beveled needle hub; and pushing said hollow plunging tube in a forward manner.

* * * * *